(12) United States Patent
Kelner et al.

(10) Patent No.: US 8,257,414 B2
(45) Date of Patent: Sep. 4, 2012

(54) THERMAL PUMPS WITH FEATURES

(75) Inventors: William J. Kelner, Tonawanda, NY (US); Thomas P. Stewart, Orchard Park, NY (US)

(73) Assignee: Stryker Corporation, Kalamazoo, MI (US)

( * ) Notice: Subject to any disclaimer, the term of this patent is extended or adjusted under 35 U.S.C. 154(b) by 1563 days.

(21) Appl. No.: 11/604,914

(22) Filed: Nov. 28, 2006

(65) Prior Publication Data
US 2008/0125839 A1 May 29, 2008

(51) Int. Cl.
*A61F 7/00* (2006.01)
(52) U.S. Cl. ........................................ 607/104
(58) Field of Classification Search ............ 607/104
See application file for complete search history.

(56) References Cited

U.S. PATENT DOCUMENTS

| | | | |
|---|---|---|---|
| 2,726,658 A | 12/1955 | Chessey | |
| 3,402,709 A | 9/1968 | Shivers et al. | |
| 4,459,468 A | 7/1984 | Bailey | |
| 4,772,778 A | 9/1988 | Ogawa | |
| 4,844,072 A | 7/1989 | French et al. | |
| 4,901,257 A | 2/1990 | Chang et al. | |
| 5,097,829 A | 3/1992 | Quisenberry | |
| 5,241,958 A | 9/1993 | Noeldner | |
| 5,266,778 A | 11/1993 | Bailey | |
| 5,336,249 A | 8/1994 | Mahawili | |
| 5,381,954 A | 1/1995 | Tokizaki | |
| 5,562,604 A | 10/1996 | Yablon et al. | |
| 5,871,526 A | 2/1999 | Gibbs et al. | |
| 5,964,092 A | 10/1999 | Tozuka et al. | |
| 6,283,931 B1 | 9/2001 | Augustine | |
| 6,517,510 B1* | 2/2003 | Stewart et al. | 604/31 |
| 6,551,348 B1 | 4/2003 | Blalock et al. | |
| 6,582,425 B2 | 6/2003 | Simpson | |
| 6,660,027 B2 | 12/2003 | Gruszecki et al. | |
| 6,818,012 B2 | 11/2004 | Ellingboe | |
| 6,840,955 B2 | 1/2005 | Ein | |
| 6,974,934 B2 | 12/2005 | Sprock et al. | |
| 7,497,870 B2 | 3/2009 | Frey et al. | |
| 2001/0039391 A1* | 11/2001 | Augustine | 602/2 |
| 2004/0210283 A1 | 10/2004 | Rose et al. | |
| 2005/0005626 A1 | 1/2005 | McMahon | |
| 2005/0015125 A1* | 1/2005 | Mioduski et al. | 607/102 |
| 2006/0195168 A1* | 8/2006 | Dunbar et al. | 607/108 |
| 2008/0195184 A1 | 8/2008 | Ziaimehr | |
| 2008/0255538 A1 | 10/2008 | Ellis | |
| 2009/0118802 A1* | 5/2009 | Mioduski et al. | 607/102 |

* cited by examiner

*Primary Examiner* — Roy Gibson
*Assistant Examiner* — Kaitlyn Smith
(74) *Attorney, Agent, or Firm* — Warner Norcross & Judd LLP

(57) ABSTRACT

The present invention is directed to a thermal pump for controlling air bubbles, thermal therapy to allow the patient to perceive that the thermal therapy is constantly being applied, and ensure the appropriate amount of water flows through the thermal pump.

29 Claims, 10 Drawing Sheets

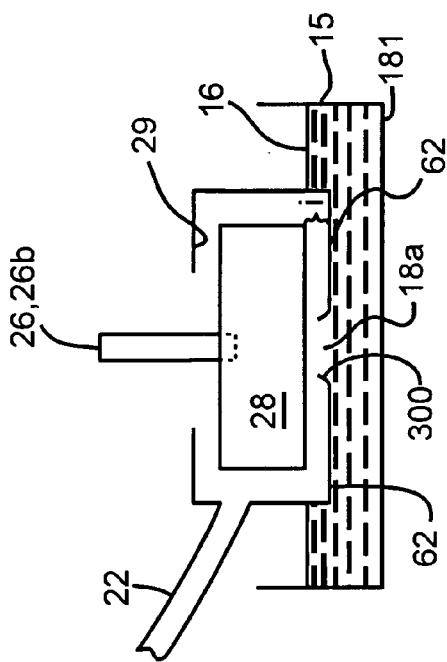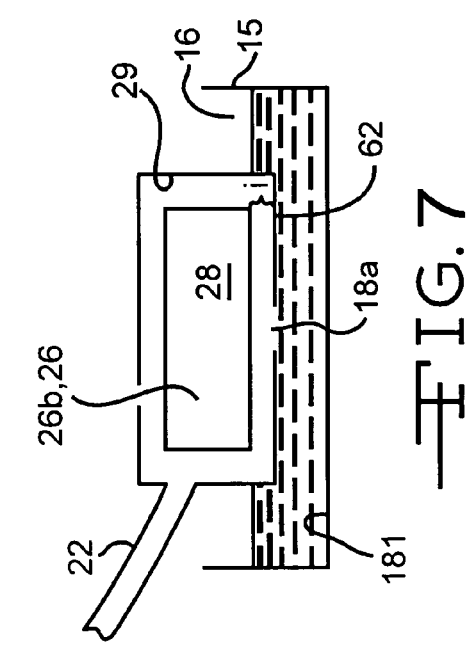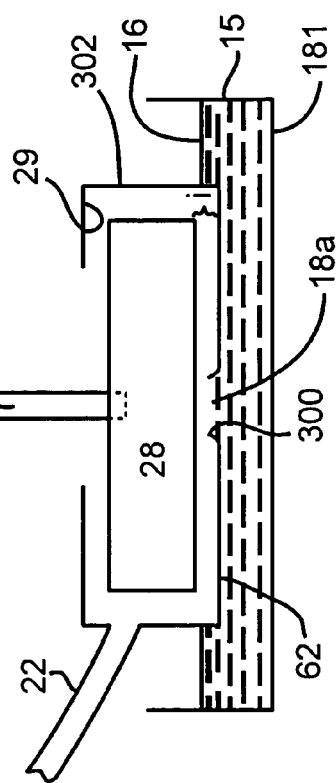
FIG. 7
FIG. 8
FIG. 9

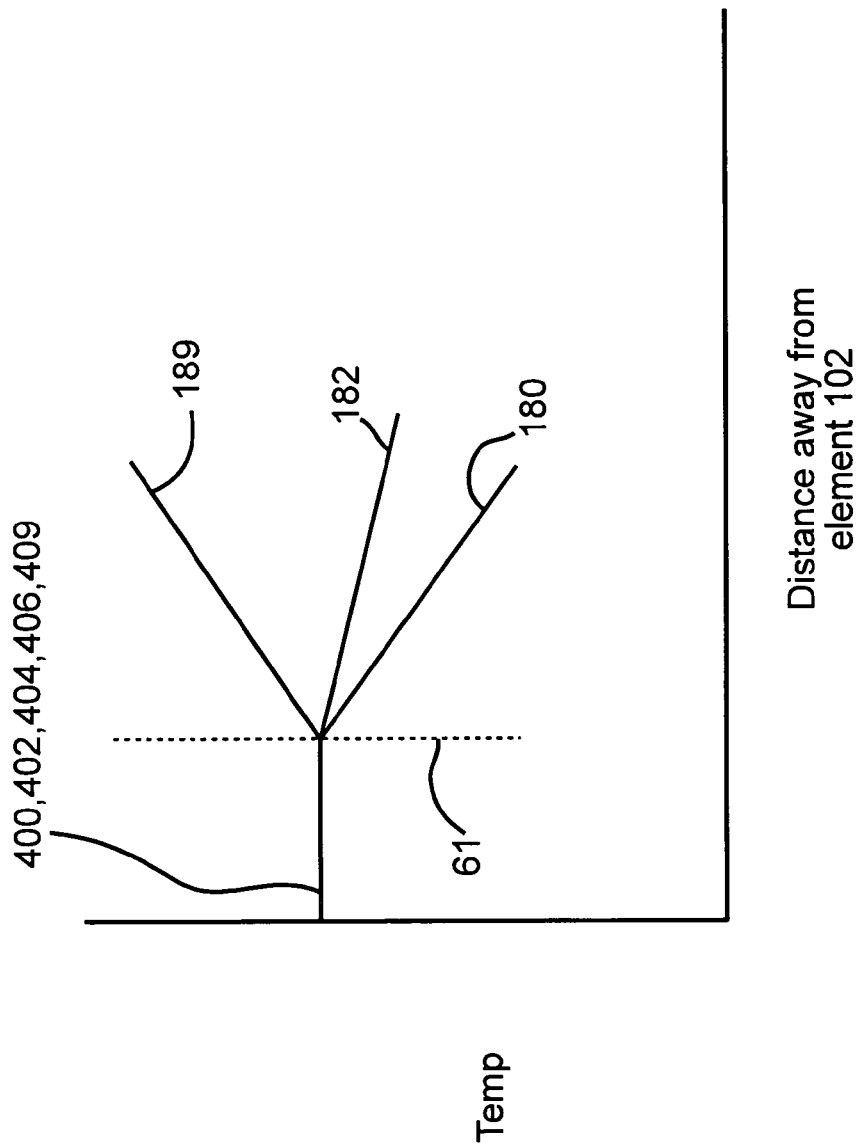

THERMAL PUMPS WITH FEATURES

FIELD OF THE INVENTION

The present invention is directed to a thermal pump.

BACKGROUND OF THE PRESENT INVENTION

Since at least 1975, Gaymar Industries, Inc. has manufactured a thermal pump. Gaymar trademarked its thermal pump 10 a T/Pump. According to Gaymar's website, the "T/Pump effectively treats muscle and joint pain, acute lower back pain, arthritis, edema, wound and post-operative drainage and dermatological conditions. It features a dual temperature setpoint scale and dependable thermistor actuated temperature controls, which allow the T/Pump to quickly set and maintain temperatures from 85° F. to 107° F. with ±2° F. at 107° F. accuracy." Maintaining the temperatures at such rates is deemed by those of ordinary skill in the art to be a constant temperature.

Gaymar also reports, "For patient safety, dual backup thermostats prevent overheating. The T/Pump system also features timesaving controls and advanced security features such as key-operated controls; an illuminated off/on switch; leak-proof connections; secure hose attachments; and a water level window." In particular, the thermal pump system 10 has a water bath 15, a pump container 20, a heater block system 100, and a patient application device 200 as illustrated in FIG. 1.

The pump container 20, as illustrated in FIGS. 2 and 3, is divided into two compartments—a dry compartment 25 and a wet compartment 29. In FIG. 2, the dry compartment 25 and the wet compartment 29 are divided by a barrier 33. The dry compartment 25 contains a motor 24. A shaft 26, in the embodiment illustrated in FIG. 2, extends between the dry compartment 25 and the wet compartment 29 through an aperture 31 of the barrier 33. An o-ring 535 is positioned around the shaft 26 and within the aperture 31 to decrease the chance of water entering the dry compartment 25 and ensure the shaft 26 is properly positioned in the aperture 31. The wet compartment 29 contains a propeller 28, a protruding water inlet 18, and a water outlet 22. The pump container 20, with the above-identified instruments, moves the water (a) from the water bath 15, (b) into the protruding water inlet 18, (c) into the wet compartment 29, and (d) then into the water outlet conduit 22. Conduit 22 directs the water from the pump container 20 into the heater block 100.

The motor 24 is normally electrically powered. The motor 24 is any conventional motor. In one embodiment the conventional motor operates on 120 Volts—alternating current, 60 Hz, 200 Watts or equivalents thereof. In addition, the motor 24 in conjunction with the remainder of the thermal pump 10 should be able to move about or more than 9 to 14 gallons per hour.

The shaft 26 has a proximal end 35 and a distal end 37. The proximal end 35 interconnects to the motor 24. The motor 24 rotates the shaft 26 a predetermined direction. In the embodiment illustrated in FIG. 2, the distal end 37 interconnects to the propeller 28 and the shaft 26 rotates the propeller 28 in the predetermined direction. Thereby the water in the water bath 15 is pulled into the wet compartment 29 through the protruding water inlet 18.

Alternative Shaft Design

An alternative version of the prior art pump container 20 is illustrated in FIG. 3 and is an electromagnetic pump system. The pump container 20 has the motor 24 and a motor shaft 26a in the dry compartment 25. The shaft's proximal end 35 interconnects to the motor shaft 26a which rotates the motor shaft 26a the predetermined direction. The motor shaft's (26a) distal end 37 has a branch, two are shown 37a, 37b. Each distal end of the branch 37a, 37b has an exterior surface 38a, 38b and those exterior surfaces are separated by a distance (x). Each branch 37a, 37b has an interior surface 39a, 39b. Each interior surface 39a, 39b has a magnetized material 40a, 40b thereon and the distance between the interior surfaces of the magnetized material 40a, 40b is the distance (y). The distance (y) is less than the distance (x).

The dry compartment 25 has a bottom end 42. The bottom end 42, and the remaining dry compartment 25, is a barrier that inhibits water from entering the dry compartment 25. The bottom end 42 has a circulation area 44 that allows the two branches 37a, 37b of the distal end 37 and the corresponding magnetized materials 40a, 40b to rotate in the predetermined direction. That means the circulation area needs an outer diameter greater than (x), and an inner diameter less than (y) to allow the magnetized branch ends rotate.

The bottom end 42 also has a female receiving area 46 for receiving a male interconnection area 48 on the top surface 49 of the wet compartment 29. The female receiving area 46 is within the inner diameter of the circulation area 44. The male interconnection area 48 and the female receiving area 46 are made of a material(s) that allows the magnetic forces of the magnetized material 40a, 40b to penetrate through.

The wet compartment 29 contains the propeller 28, a propeller shaft 26b wherein the distal end 52 of the propeller shaft 26b interconnects to the propeller 28 and the proximal end 54 of the propeller shaft 26b extends toward the motor shaft 26a in the interconnection area 48. On the propeller shaft 26b are magnetized materials 56a, 56b that correspond with the motor shaft's 26a magnetized material-40a, 40b. That way, when the motor shaft's 26a rotates the predetermined direction the propeller shaft 26b also rotates in the predetermined direction through the magnetized materials 40a to 56a and 40b to 56b. Which means the propeller 28 rotates in the predetermined direction. This embodiment allows the dry compartment 25 to remain dry without any apertures.

Pushing Water

Whichever prior art pump container 20 embodiment is used, the thermal pump 10 operates properly when the protruding water inlet 18 is immersed in the water in the water bath 15 as illustrated in FIGS. 1, 2 and 3 or positioned below the water line 16 in the water bath 15 and away from water bath 15 as illustrated in FIG. 4. Those positions allow the protruding water inlet 18 to allegedly self-prime. In both embodiments, the protruding water inlet 18 protrudes from the pump container 20. The water is pulled into the wet compartment 29 by the rotation of the propeller 28. The propeller's rotation pushes the water into the conduit 22 toward the heater block 100.

Heater Block

The heater block 100 can be within the dry compartment 25 or not. The heater block 100 contains conventional heating elements 102 interconnected to a conventional thermal control system 106 as illustrated in FIGS. 5 and 6. The thermal control system 106 can be a manual thermostat; proportional, integral, derivative (PID) temperature controller; a thermistor actuated temperature controls; a digital thermostat; or equivalents thereof that control the amount of electricity that runs through the heating elements 102 to obtain the desired and/or programmed temperature. As previously stated, the heater block 100 warms the water to a desired temperature and once the water reaches that desired temperature the water's temperature, for all intents and purposes, remains constant.

The heater block 100 can also have a dual temperature set-point scale 104 interconnected to the thermal control system 106. The temperature set-point scale 104 allows the thermal pump 10 to be quickly set and maintain temperatures from 85° F. to 107° F. with ±2° F. at 107° F. accuracy. The set-point scale is positioned on one side of line 190 because those elements on that side of line 190 are controllable by the operator without dismantling the thermal pump 10. The heater block 100 can also have a timing mechanism 177 positioned between the thermal control system 106 and the heating elements 102 as illustrated in FIG. 5. The timing mechanism 177 turns the heating elements 102 off after a predetermined time frame.

Another feature of the heater block 100 in conjunction with the thermal energy pump 10 is that there is a tip sensor/alarm 110. The tip alarm 110 transmits a signal 111 when the tip alarm 110 senses the thermal device 10 has been tipped. That signal 111 is transmitted to the thermal control system 106, or equivalent thereof, to shut the heating elements 102 off. That way, the heating elements 102 do not melt the thermal device 10.

Patient Application

From the heater block 100, the heated water is directed into a conduit 202. Conduit 202 directs the heated water into the patient application device 200. The patient application device 200 can be a cushion, a blanket, a wrap-around unit, a tub, drip applicator, and/or body core adjusting device. Examples of such devices 200 include and are not limited to Gaymar's T-pads, convective products, and conductive products. The device 200 can re-circulate the water into the water bath 15 through conduit 204 as illustrated in FIG. 1 or alternatively release the water into the environment.

SUMMARY OF THE INVENTION

The present invention is directed to a thermal pump for controlling air bubbles, thermal therapy to allow the patient to perceive that the thermal therapy is constantly being applied, and ensure the appropriate amount of water flows through the thermal pump.

BRIEF DESCRIPTION OF THE FIGURES

FIGS. 7 to 9 illustrate different versions of a thermal pump system's wet compartment and water inlet.

FIG. 14 illustrates a graph of the temperature of the water as proceeds away from the heating elements.

DETAILED DESCRIPTION OF THE PRESENT INVENTION

Figure 2:
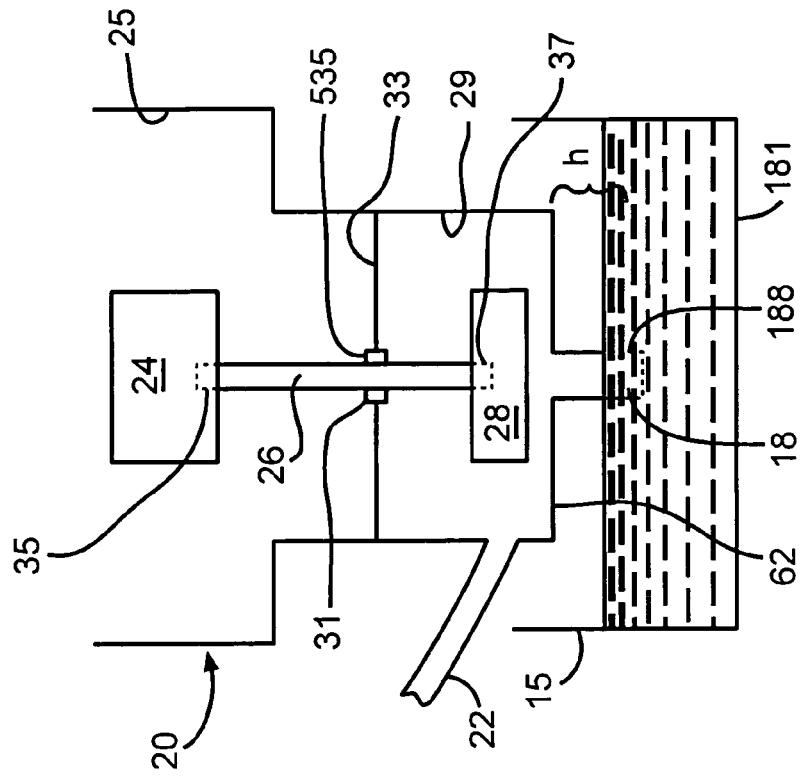
FIG. 2 illustrates a prior art cross-sectional view of FIG. 1 for the pump container unit.
Figure 1:
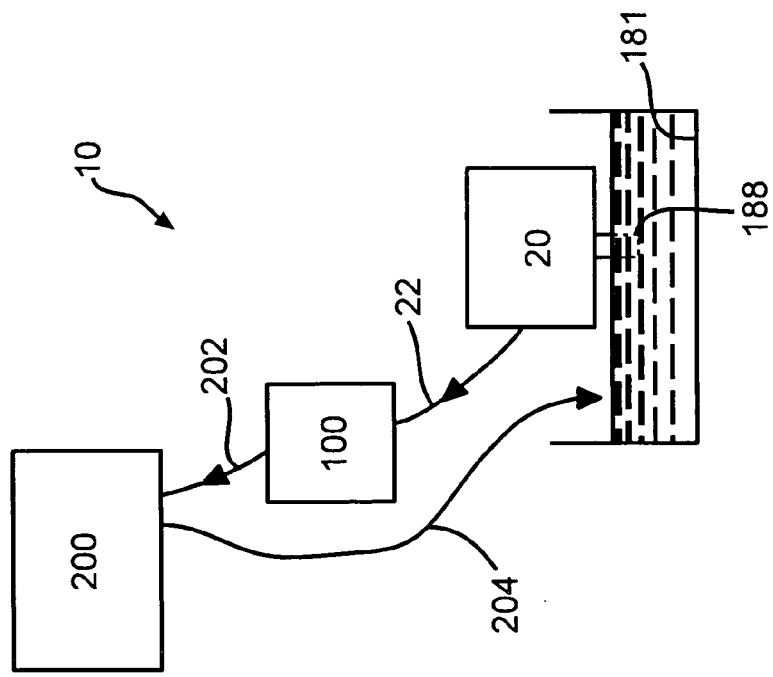
FIG. 1 illustrates an overall schematic of a prior art thermal pump system.
Figure 4:
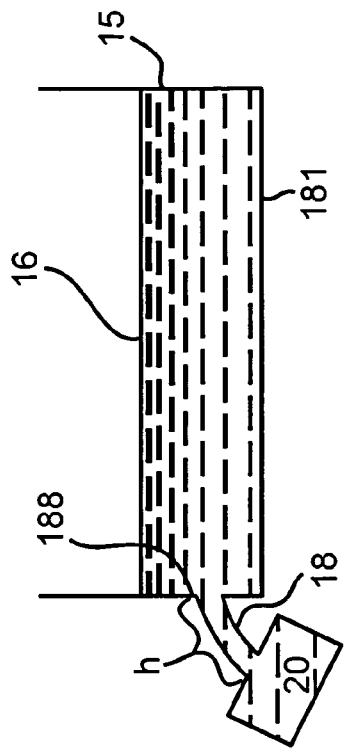
FIG. 4 illustrates a prior art alternative embodiment of a protruding water inlet system.
Figure 3:
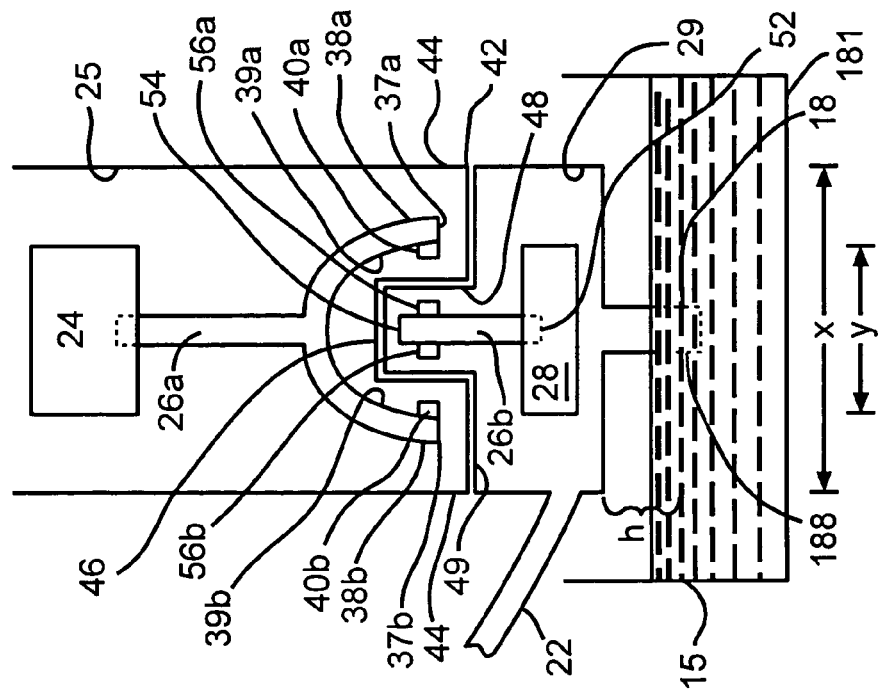
FIG. 3 illustrates a prior art alternative embodiment of FIG. 2.
Figure 5:
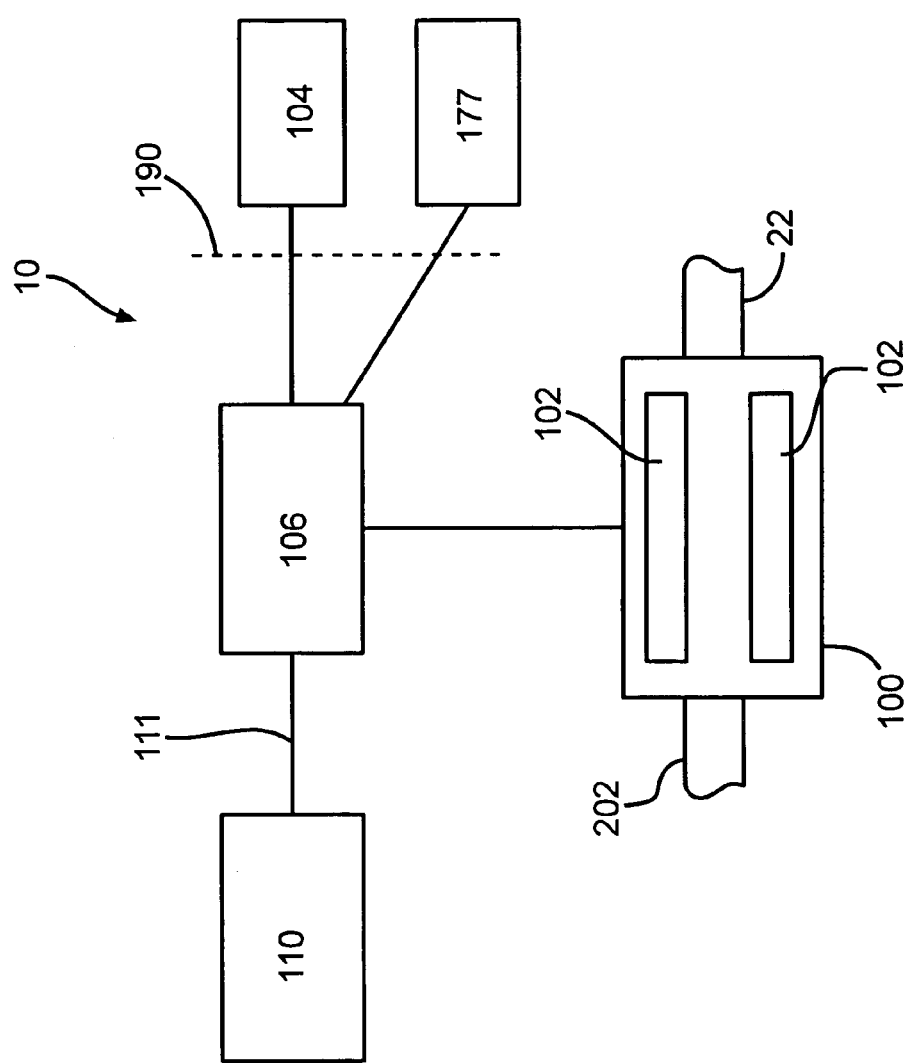
FIGS. 5 and 6 illustrate portions of prior art schematics of control system embodiments of the thermal pump systems.
Figure 6:
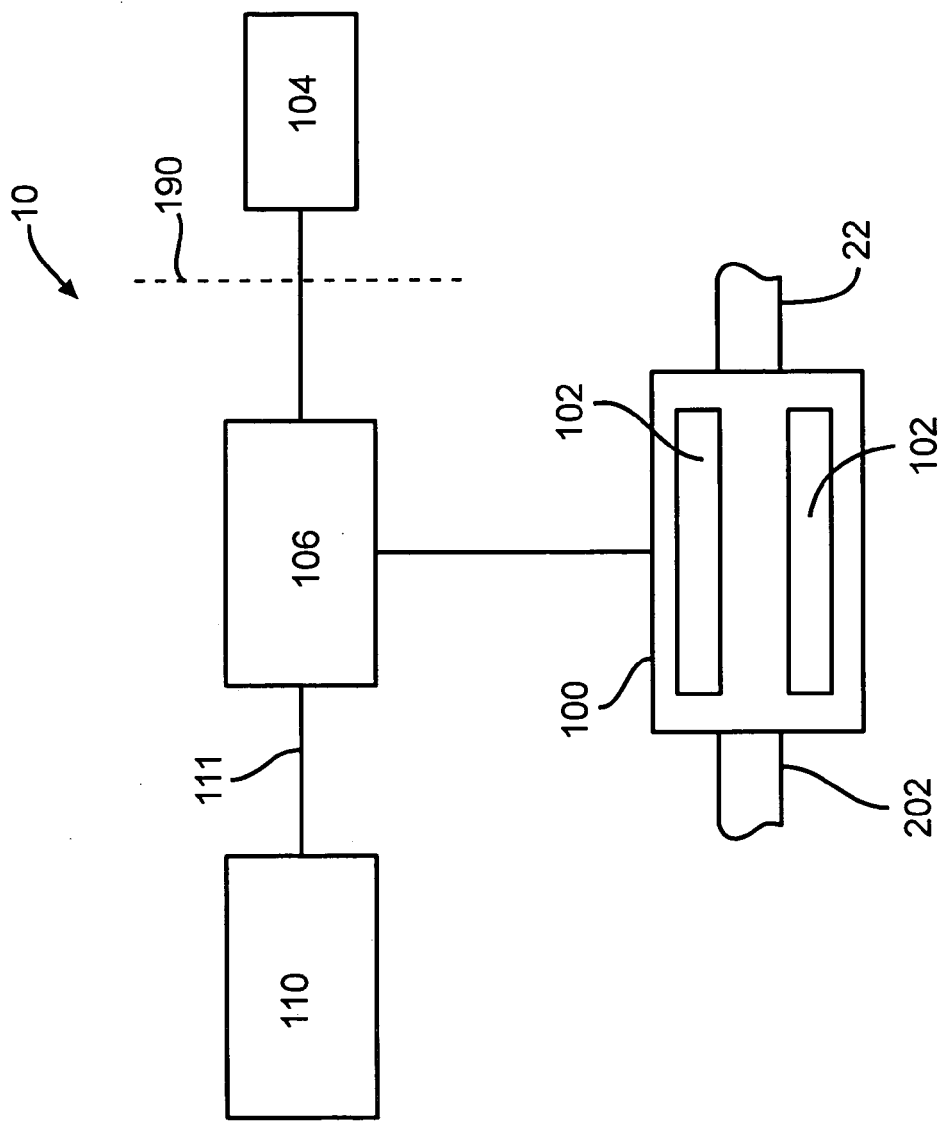

The present invention alters certain embodiments of the thermal pump system 10 to maximize efficiency, safety, and effectiveness to patients and the operators. There are numerous ways to improve the thermal pump system 10 and those ways are categorized as follows:

A. Decreased Air Bubbles

The prior art thermal pump system 10 utilizes the protruding water inlet 18 that protrudes from pump container 20. The protruding water inlet 18 poses potential problems when the protruding water inlet 18 is not properly primed. One of those potential problems is that an air bubble can be caught in the protruding water inlet 18. The caught air bubble inhibits the water from entering into the wet compartment 29 even when the propeller 28 operates. And if the thermal pump 10 is operating and insufficient water enters into the heating block 100, the heating block has been known to melt portions of the thermal pump 10. This potential problem should be avoided.

To address this potential problem, the inventors have altered the structure of the protruding water inlet 18. As illustrated in FIG. 7, the aperture water inlet 18a does not protrude from the pump container 20. Instead the aperture water inlet 18a is an aperture that is planar with the bottom surface 62 of the pump container 20, in particular the wet compartment 29 as illustrated in FIG. 7, or has an extension 300 that intrudes into the wet compartment 29 as illustrated in FIG. 8. These two embodiments can be used only when the wet compartment's bottom surface 62 is in the water bath 15 and not contacting the bottom surface 181 of the water bath 15. Moreover, these two embodiments decrease the chance of air bubbles inhibiting the water from flowing into the wet compartment 29.

The air bubbles are decreased for numerous reasons. One reason is that the aperture water inlet 18a is a distance (i) from the propeller 28 as illustrated in FIGS. 7, 8 and 9 while the distal part 188 of the protruding water inlet 18 in the prior art embodiments is a distance (h) from the propeller 28. The distance (h) is greater than the distance (i). That means there is less chance of an air bubble getting caught in the aperture water inlet 18a.

And if air bubbles happen to enter into the wet compartment 29, the wet compartment 29 can have a bubble release aperture 302, as illustrated in FIG. 9, to release the air bubble from the wet compartment 29. The bubble release aperture 302 is positioned at or near the upper portion of the wet compartment 29. That way the air bubbles that enter the wet compartment 29 are released from the wet compartment 29 with a decreased chance of entering the conduit 22 and blocking the aperture water inlet 18a.

By decreasing the chance of the air bubbles entering the wet compartment 29, the conduit 22, and the heating block 100, Gaymar has decreased the chance of diminished water flow into the heating block 100. As previously indicated if there is a diminished water flow into the heating block 100, the heating block 100 can overheat and cause problems in the thermal pump system 10. Such results are undesirable and the present invention decreases the chances of those undesirable results.

B. Time Therapy

Patients after a certain time frame do not believe that constant temperature heated water therapy is applying thermal energy to them when it is.

Figure 10:
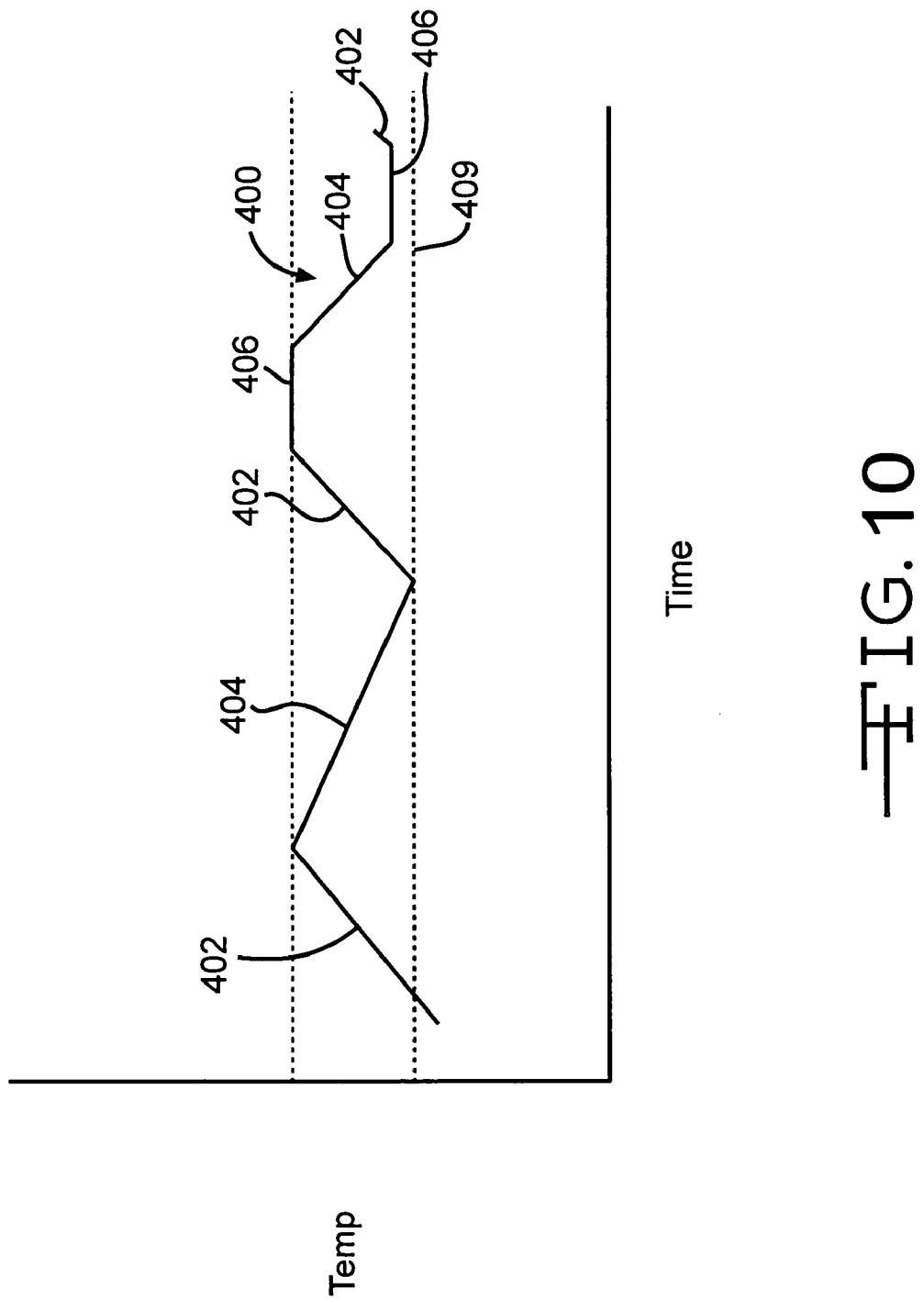
FIG. 10 illustrates a graph of altering the temperature of the water in the present invention.

To address this psychological patient issue, Gaymar has devised a time therapy protocol for the heating block 100. The time therapy protocol is illustrated in FIG. 10. The protocol calls for heating 402 the water for a predetermined time frame until it reaches the predetermined temperature 400. The heating step 402 is designed to allow the patient to feel the heated water is applying thermal energy through the patient application device 200 to them. An example of the sensed heating rate 402 is more than 1.5 degrees Fahrenheit per minute. Once the water temperature reaches the predetermined temperature 400, the heater block 100 begins to decrease the temperature of the water at a rate that cannot be sensed by the patient 404. An example of the non-sensed decrease rate 404 is 0.01 to about 2.0 degrees Fahrenheit per minute for a time period longer than the sensed heating rate and not below a predetermined low threshold 409. The predetermined low threshold 409 can be about 5 to 25, preferably 8 to 15, degrees below the predetermined temperature 400. The heating step 402 is repeated within the time frame for the thermal therapy protocol to the patient.

Alternatively, the heater block 100 can maintain the water's temperature 406 for a predetermined time frame after reaching the predetermined temperature 400 and then begin the non-sensed decreased temperature protocol 404.

Figure 11:
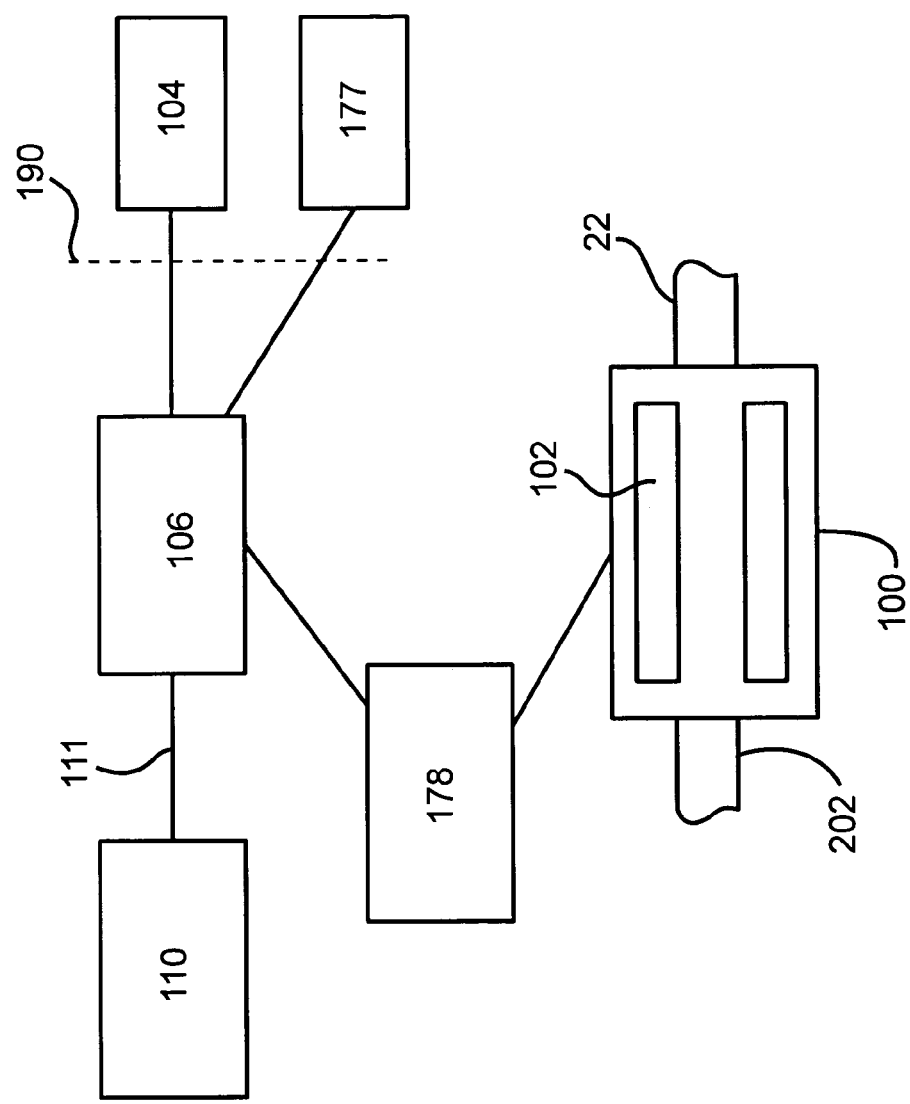
FIG. 11 illustrates a schematic of a portion of the control system for the thermal pump system of the present invention.

Unlike the time therapy device 177 disclosed in the prior art, this embodiment of the present invention has a therapy management device 178 within the internal section of the thermal pump 10 as illustrated in FIG. 11. The therapy management device 178 controls the duration and the rate in which the heating elements increase heat (line 402 in FIG. 10), decrease heat (line 404 in FIG. 10; which includes shutting down the heating elements 102 and/or turning down the temperature of the heating elements 102), and in some embodiments maintaining the thermal energy (lines 400 or 409; or anywhere in-between lines 400 and 409 in FIG. 10). The therapy management device 178 can be a part of the thermal control system 106 or not.

This embodiment allows the patient to periodically assume that the patient application device 200 is applying the desired thermal energy. That way, the patient is expected to retain the patient application device 200 on them for the designated and desired time frame, which in turn should produce the desired results.

C. Water Flow Control

Figure 13:
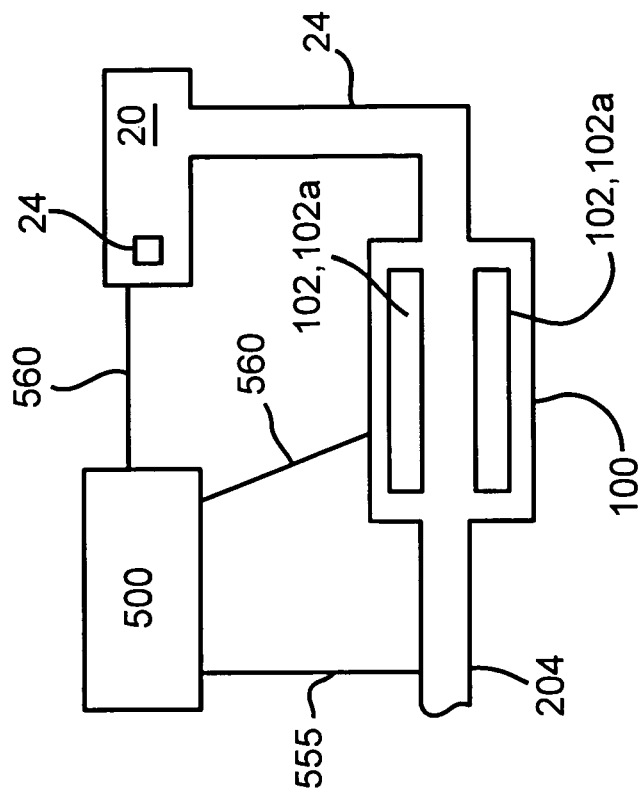
FIGS. 12 and 13 illustrate a schematic of another portion of the control system for the thermal pump system of the present invention.
Figure 12:
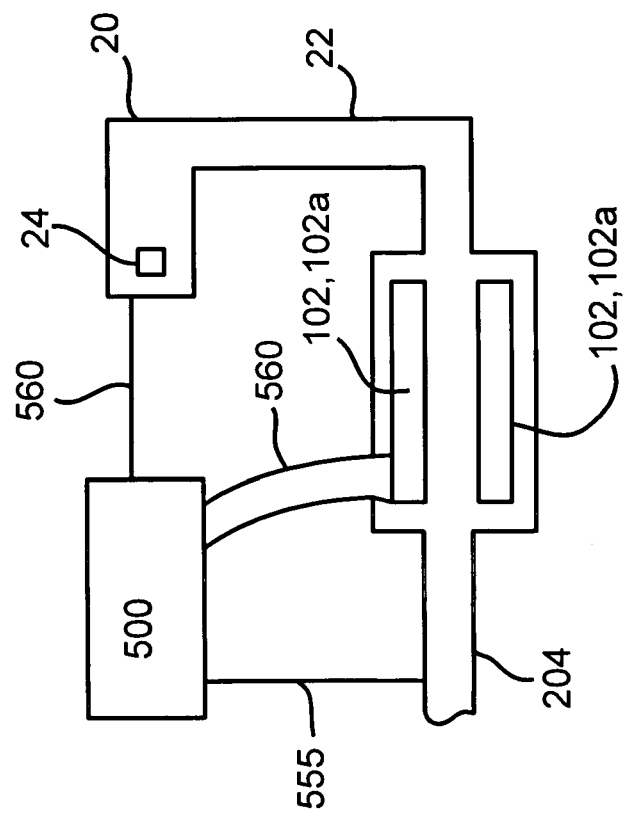

The pump system 10 can also have a water flow monitor 500. The water flow monitor 500 is within the heater block 100 as illustrated in FIG. 12 or the conduit 202 from the heater block 100, as illustrated in FIG. 13. The water flow monitor 500 measures the water's temperature and the surrounding area. The water's temperature and the temperature surrounding area of the water flow monitor 500 at the certain location determine if the pump container 20 is pumping sufficient amounts of water into the heater block 100.

If the water flow monitor 500 is in the conduit 202, the water flow monitor will measure 555 the temperature of the heated water and the area surrounding the water flow monitor. As the heated water proceeds away from the heater element 102, the heated water will naturally decrease in temperature. That is a law of nature and is not being claimed in this application. Instead, the present invention capitalizes on this law of nature to determine if the pump container 20 is pumping sufficient amounts of water into the heater block 100. FIG. 14 illustrates (a) the point 167 at which the heated water proceeds away from the heater element 102; (b) the temperature of the heated water as it proceeds away from the heater element 102 at a temperature previously identified as values 400, 402, 404, 406, or 409 as illustrated in FIG. 10; and (c) the temperature of the heated water as it proceeds away from the heater element 102 changes. The water flow monitor's 500 measurements of the heated water's temperature should proceed down line 180, or equivalent thereof, in FIG. 14 if there is sufficient enough water flowing through the heating block 100. Alternatively, if the water flow is still flowing but insufficient for optimum operation of the thermal pump 10 (possible kink in tubing or patient application device 200; or low water), then the water flow monitor's 500 measurements of the heated water's temperature should proceed down line 182, or equivalent thereof, in FIG. 14. And if the water flow has ceased, then the water flow monitor's 500 measurements of the heated water's temperature should proceed down line 184, or equivalent thereof, in FIG. 14.

If the water flow monitor's 500 measurements are between lines 182 and 184, monitor 500 transmits a shut down signal 560 to the heating block 100 and the pump container 20 as illustrated in FIGS. 12 and 13. By shutting both the heating block 100 and the pump container 20, the fluid in the patient application device 200 does not provide a reverse thermal energy therapy to the patient, which can be deleterious if the desired applied thermal energy is to be heated.

D. Alternative Embodiment

In some cases, it may be desired for the pump system 10 to provide cool thermal energy. In those embodiments, the water in the water bath 15 contains water with ice. Unlike the prior embodiments, the ice is designed to fit into the water bath 15. And unlike the prior art pump systems 20, the pump with the aperture inlet design 18a has a decreased chance of getting clogged with ice in relation to the protruding water inlet 18. The aperture inlet design 18a has a decreased chance because the aperture inlet design 18a is positioned in the water of the water bath 15 and since ice floats there is a decreased chance that the ice would block the aperture inlet design 18a. Accordingly, cold water can be utilized in the present invention.

Figure 15:
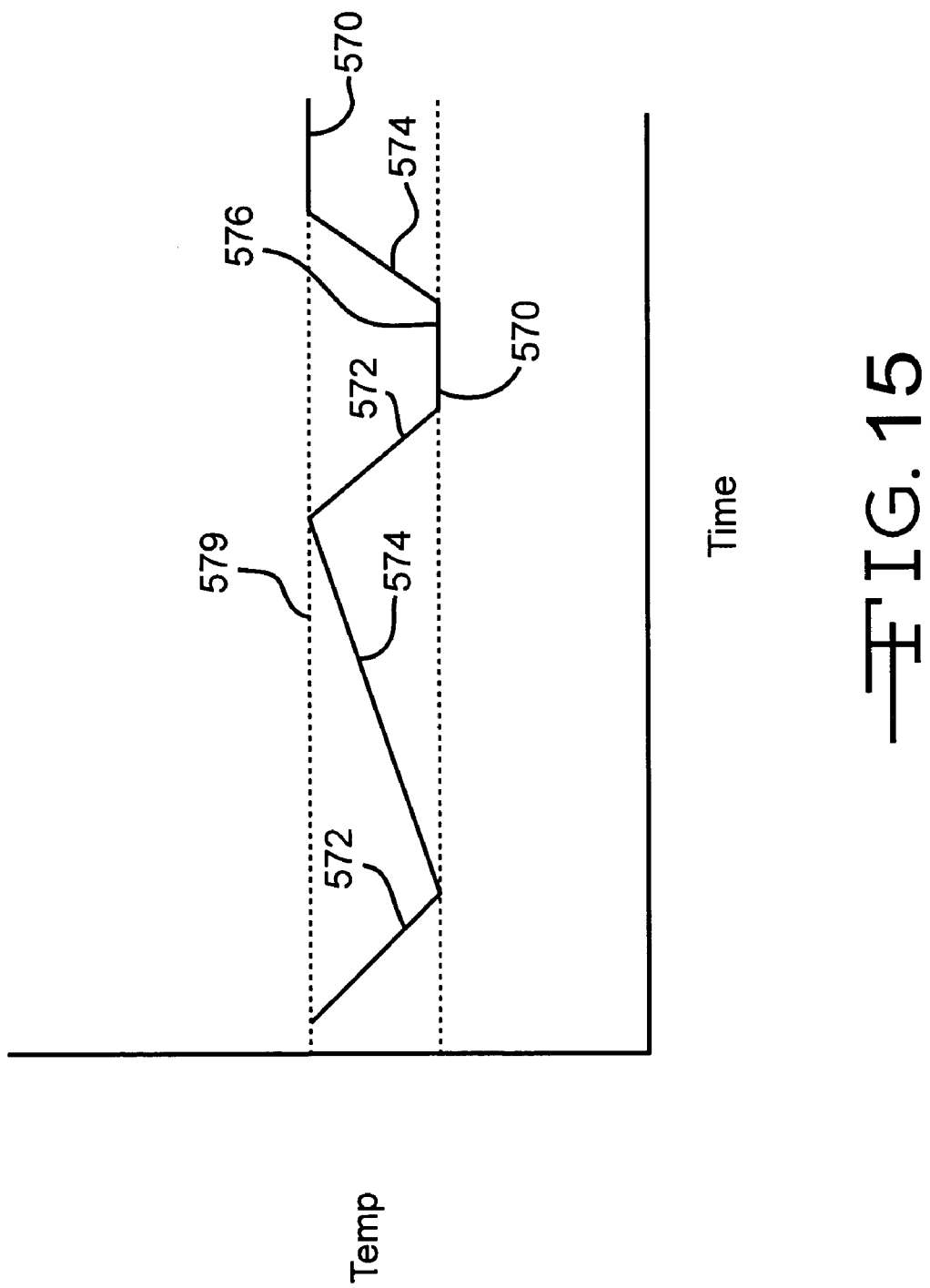
FIG. 15 illustrates a temperature graph of an embodiment of the present invention.

Like the psychological heating therapy system, Gaymar has devised a time therapy protocol for the heating block 100 in relation to cooling the patient. The time therapy protocol is illustrated in FIG. 15. The protocol calls for cooling 572 the water for a predetermined time frame until it reaches the predetermined temperature 570. The cooling step 572 is designed to allow the patient to feel the cooled water is applying thermal energy through the patient application device 200 to them. An example of the sensed cooling rate 572 is more than 1.5 degrees Fahrenheit per minute. Once the water temperature reaches the predetermined temperature 570, the heater block 100 begins to increase the temperature of the water at a rate that cannot be sensed by the patient 574. An example of the non-sensed decrease rate 574 is 0.01 to about 2.0 degrees Fahrenheit per minute for a time period longer than the sensed cooling rate and not below a predetermined high threshold 579. The predetermined high threshold 579 can be about 5 to 25, preferably 8 to 15, degrees above the predetermined temperature 570. The cooling step 572 is repeated within the time frame for the thermal therapy protocol to the patient.

Alternatively, the heater block 100 can maintain the water's temperature 576 for a predetermined time frame after reaching the predetermined temperature and then begin the non-sensed increased temperature protocol 574.

In addition, the heater block 100 can have cooling pads 102a, instead of heating pads 102, to cool the water to the desired temperature.

Unlike the time therapy device 177 disclosed in the prior art, this embodiment of the present invention has a therapy management device 178 within the internal section of the thermal pump 10 as illustrated in FIG. 12. The therapy management device 178 controls the duration and the rate in which the heating elements allow the decrease of heat (line 572 in FIG. 15; which includes shutting down the heating elements 102 and/or turning down the temperature of the heating elements 102), increase heat (line 574 in FIG. 15), and in some embodiments maintaining the thermal energy (lines 570 or 579, or anywhere in-between lines 570 and 579 in FIG. 15). The therapy management device 178 can be a part of the thermal control system 106 or not.

This embodiment allows the patient to periodically assume that the patient application device 200 is applying the desired thermal energy. That way, the patient is expected to retain the patient application device 200 on them for the designated and desired time frame, which in turn should produce the desired results.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

We claim:

1. A thermal pump system comprising:
a pump container having a dry compartment that contains a motor, a wet compartment that contains a propeller, and a shaft system that interconnects the motor to the propeller;
the wet compartment has a water inlet;
the propeller pulls water from a water bath into the wet compartment through the water inlet and pushes the water into a conduit toward a heating block and to a patient application device;
the heating block has a heating pad and/or a cooling pad; and
a therapy management device that controls the thermal energy provided by the heating pad and/or the cooling pad to
(a) direct the water's temperature toward a first predetermined temperature at a first rate that can be sensed by a patient when the patient application device is applied to the patient, wherein the first rate is more than 1.5 degrees Fahrenheit per minute,
(b) direct the water's temperature toward a second predetermined temperature at a second rate that is not normally sensed by the patient when the patient application device is applied to the patient, wherein the second rate has a magnitude less than said first rate, and wherein
(i) if the first predetermined temperature is obtained by raising the water's temperature then the second predetermined temperature is obtained by lowering the water's temperature and
(ii) if the first predetermined temperature is obtained by lowering the water's temperature then the second predetermined temperature is obtained by raising the water's temperature; and
(c) repeat step (a).

2. The thermal pump system of claim 1 wherein the water inlet does not protrude away from the pump container.

3. The thermal pump system of claim 1 wherein the heating block has a heating pad that warms the water.

4. The thermal pump system of claim 1 wherein the heating block has a cooling pad that cools the water.

5. The thermal pump system of claim 1 wherein between step (a) and step (b), the heating block maintains the water's temperature at the first predetermined temperature for a predetermined time frame.

6. The thermal pump system of claim 5 wherein the predetermined time frame ranges from 0 seconds to 10 minutes.

7. The thermal pump system of claim 5 wherein the difference between the first predetermined temperature and the second predetermined temperature ranges from 5 to 25 degrees Fahrenheit, and wherein the second rate is 0.01 to about 2.0 degrees Fahrenheit per minute.

8. The thermal pump system of claim 1 wherein between step (b) and step (c), the heating block maintains the water's temperature at the second predetermined temperature for a predetermined time frame.

9. The thermal pump system of claim 1 wherein the shaft system is a single shaft.

10. The thermal pump system of claim 1 wherein the shaft system comprises a first shaft positioned exclusively in the dry compartment and having a first proximal end and a first distal end wherein the first proximal end connects to the motor and the first distal end (a) extends toward the propeller and (b) has a first magnet, and a second shaft positioned exclusively in the wet compartment and having a second proximal end and a second distal end wherein the second proximal end connects to the propeller and the second distal end (a) extends toward the motor, and (b) has a second magnet.

11. The thermal pump system of claim 1 wherein the difference between the first predetermined temperature and the second predetermined temperature ranges from 5 to 25 degrees Fahrenheit.

12. A thermal pump system comprising:
a pump container that contains a propeller that pushes water toward a heating block and to a patient application device;
the heating block has a heating pad and/or a cooling pad; and
a therapy management device that controls the thermal energy provided by the heating pad and/or the cooling pad to
(a) direct the water's temperature toward a first predetermined temperature at a first rate that can be sensed by a patient when the patient application device is applied to the patient,
(b) direct the water's temperature toward a second predetermined temperature at a second rate that is not normally sensed by the patient when the patient application device is applied to the patient, wherein the second rate is 0.01 to about 2.0 degrees Fahrenheit per minute and the second rate has a magnitude less than the first rate, and wherein
(i) if the first predetermined temperature is obtained by raising the water's temperature then the second predetermined temperature is obtained by lowering the water's temperature and
(ii) if the first predetermined temperature is obtained by lowering the water's temperature then the second predetermined temperature is obtained by raising the water's temperature; and
(c) repeat step (a).

13. The thermal pump system of claim 12 wherein the pump container has a dry compartment that contains a motor, a wet compartment that contains the propeller, and a shaft system that interconnects the motor to the propeller;
the wet compartment has a water inlet; and
the propeller pulls water from a water bath into the wet compartment through the water inlet and pushes the water into a conduit toward the heating block and to the patient application device.

14. The thermal pump system of claim 13 wherein the water inlet does not protrude away from the pump container.

15. The thermal pump system of claim 12 wherein the heating block has a heating pad that warms the water.

16. The thermal pump system of claim 12 wherein the heating block has a cooling pad that cools the water.

17. The thermal pump system of claim 12 wherein the first rate is more than 1.5 degrees Fahrenheit per minute 18. The thermal pump system of claim 12 wherein between step (a) and step (b), the heating block maintains the water's temperature at the first predetermined temperature for a predetermined time frame.

19. The thermal pump system of claim 18 wherein the predetermined time frame ranges from 0 seconds to 10 minutes.

20. The thermal pump system of claim 12 wherein between step (b) and step (c), the heating block maintains the water's temperature at the second predetermined temperature for a predetermined time frame.

21. The thermal pump system of claim 12 wherein the difference between the first predetermined temperature and the second predetermined temperature ranges from 5 to 25 degrees Fahrenheit.

22. A thermal pump system comprising:
   a pump container that contains a propeller that pushes water toward a heating block and to a patient application device;
   the heating block has a heating pad and/or a cooling pad; and
   a therapy management device that controls the thermal energy provided by the heating pad and/or the cooling pad to
   (a) direct the water's temperature toward a first predetermined temperature at a first rate that can be sensed by a patient when the patient application device is applied to the patient, wherein the first rate is more than 1.5 degrees Fahrenheit per minute,
   (b) direct the water's temperature toward a second predetermined temperature at a second rate that is not normally sensed by the patient when the patient application device is applied to the patient, said second rate having a magnitude less than said first rate, wherein
      (i) if the first predetermined temperature is obtained by raising the water's temperature then the second predetermined temperature is obtained by lowering the water's temperature and
      (ii) if the first predetermined temperature is obtained by lowering the water's temperature then the second predetermined temperature is obtained by raising the water's temperature; and
   (c) repeat step (a).

23. The thermal pump system of claim 22 wherein the heating block has a heating pad that warms the water.

24. The thermal pump system of claim 23 wherein between step (a) and step (b), the heating block maintains the water's temperature at the first predetermined temperature for a predetermined time frame.

25. The thermal pump system of claim 24 wherein the pump container has a dry compartment that contains a motor, a wet compartment that contains the propeller, and a shaft system that interconnects the motor to the propeller;
   the wet compartment has a water inlet; and
   the propeller pulls water from a water bath into the wet compartment through the water inlet and pushes the water into a conduit toward the heating block and to the patient application device.

26. The thermal pump system of claim 25 wherein the water inlet does not protrude away from the pump container.

27. The thermal pump system of claim 24 wherein the predetermined time frame ranges from 0 seconds to 10 minutes.

28. The thermal pump system of claim 22 wherein the heating block has a cooling pad that cools the water.

29. The thermal pump system of claim 22 wherein between step (b) and step (c), the heating block maintains the water's temperature at the second predetermined temperature for a predetermined time frame.

* * * * *